United States Patent [19]

Schwartz, deceased

[11] Plant 4,293

[45] Aug. 15, 1978

[54] ROSE PLANT

[75] Inventor: Ernest Schwartz, deceased, late of Kingsville, Md., by Hazel E. Schwartz, executrix

[73] Assignee: F. Harmon Saville Nor'East Miniature Roses, Rowley, Mass.

[21] Appl. No.: 854,513

[22] Filed: Nov. 25, 1977

[51] Int. Cl.[2] ..... A01H 5/00

[52] U.S. Cl. ..... Plt./10

[58] Field of Search ..... Plt./10

*Primary Examiner*—Robert E. Bagwill
*Attorney, Agent, or Firm*—Vincent G. Gioia

[57] ABSTRACT

A novel rose variety of the miniature rose class characterized by unusual coloring contrasting scarlet red petals and dark yellow stamens which produce a yellow eye substantially as shown and described.

1 Drawing Figure

1

The present invention relates to a new and distinct variety of rose plant of the miniature rose class, which was originated by my crossing as seed parent the floribunda rose known as "Zorina" and the miniature rose known as "Magic Carousel" as pollen parent.

Among the novel characteristics possessed by this new variety which distinguish it from its parents and all other varieties of which I am aware are: (1) blooms of unusual coloring combining deep scarlet petal color with yellow point of attachment to produce a "yellow eye", (2) flowers borne primarily singly to a stem but in large quantities giving impression of continuous bloom, and (3) flowers of few petals opening quickly to display the scarlet red background for the yellow eye. Asexual reproduction by budding of the new variety as performed in Essex County, Mass., shows that the foregoing and other distinguishing characteristics come true to form and are established and transmitted through succeeding propagations.

The new and improved rose variety which I have developed is an unusual color break in a miniature rose. The combination of intense scarlet red petals provide a contrasting background for the yellow color at the base of the petals and the dark yellow stamens. Because the flowers are few-petalled and open quickly, the novel flower coloring is a prominent feature of the plant. Despite the quick opening flowers the plant gives the impression of being continually in bloom because the flowers repeat quickly. The plant itself is attractive in combining glossy foliage with well branching symmetrical growth.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "44B" is plate 44B of the Royal Horticultural Society Color Chart.

Parentage: Seedling.

*Seed parent.*—"Zorina" (floribunda).

*Pollen parent.*—"Magic Carousel" (miniature).

Class: Miniature.

2

The following observations are made of specimens grown outdoors with 30% shade in Essex County, Mass., during the month of October.

1. FLOWER

Blooming habit: Continuous, very floriferous.

A. Bud:

(1) *Size.*—Medium.

(2) *Form.*—Long pointed.

(3) *Color.*—When sepals first divide and as they begin to unfurl — near to 44B.

(4) *Sepals.*—Very long, slightly foliated, slender.

(5) *Peduncle.*—Length — normal. Aspect — sturdy and in proportion to bloom size. Strength — sufficient to hold bloom erect. Color — 143C.

B. Bloom:

(1) *Size.*—Average size when fully expended — about 1⅜ to 1½ inches.

(2) *Borne.*—Primarily singly.

(3) *Form.*—Long pointed, opening flat.

(4) *Petalage.*—Number of petals under normal conditions — about 10 to 12.

(5) *Color (during first 2 days).*—Outer petals — 44B with very slight yellow undertone or influence but the color intensity is deepened by what appears to be black coloring influence. Inner petals at center of flower and base of petals (point of attachment) — slight lightening at base to become 15B at point of attachment but yellow coloring extends somewhat beyond point of attachment to give the appearance, together with the dark yellow stamens, of a "yellow eye". Reverse of petals — 46A shading to 46C. Generally tonality from a distance — deep scarlet with "yellow eye".

(6) *Color change.*—As bloom ages — blues a little shading to 46B proceeding to general tonality of crimson with "yellow eye".

C. Petals:

(1) *Texture.*—Thick, firm.

(2) *Appearance.*—Inside — velvety; Outside — Matte with occasional white streaks on outer petals.

(3) *Form.*—Fan shaped, on reflexing appearing pentagonal or diamond shaped.

(4) *Arrangement.*—Regularly arranged, shingle-like.

(5) *Petaloids in center.*—Virtually none although when present often have yellow streak.
(6) *Persistence.*—Drop off cleanly.
(7) *Fragrance.*—Light and sweet.
(8) *Lasting quality.*—Long enough that with continuous blooming habit gives impression that plant is always covered in blooms.

2. REPRODUCTIVE ORGANS

A. Stamens, filaments and anthers:
(1) *Arrangement.*—Regularly arranged and abundant.
(2)*Color.*—17A.
B. Pollen: Color — 23A.
C. Styles: Even, 2D.
D. Stigmas: Color — 2D.
E. Hips: None.

3. PLANT

A. Form: Compact.
B. Growth: Vigorous, branching symmetrical. Height attained — 15 to 18 inches.
C. Foliage: Compound 5 to 7 leaflets.
(1) *Size.*—Medium.
(2) *Quantity.*—Abundant.
(3)*Color.*—New foliage: (sometimes with bronze margin on very young foliage). Upper side — near to 131B. Under side — near to and 138C. Old Foliage — same as new foliage.
(4) *Shape.*—Oval, pointed.
(5) *Texture.*—Upper side — glossy. Under side — matte.

(6) *Edge.*—Serrated.
(7) *Serration.*—Deeper toward point.
(8) *Leaf stem.*—Color — near to 165A. Under side — 165C.
(9) *Stipules.*—Slightly bearded.
(10) *Resistance to disease.*—Blackspot — normal. Mildew — normal.
D. Wood:
(1) *New wood.*—Color — near 143C. Bark — smooth.
(2) *Old wood.*—Color — 143B. Bark — smooth, sometimes striated.
E. Thorns:
(1) *Thorns.*—Quantity: few on many stalks, some lateral with thorns. Form — needle shaped, straight. Length — long, thin. Color — variable, off-white to reddish-brown. Position — irregular.
(2) *Prickles.*—None or few.
F. Winter hardiness: Good, requires only normal winter protection.

I claim:

1. A new and distinct variety of rose plant of the miniature class, substantially as shown and described, characterized particularly by the unusual coloring which contrasts scarlet red petals of quickly opening flowers with yellow coloring at the base of the petals that, together with dark yellow stamens produce a yellow eye on a vigorous, compact growing plant that blooms profusely.

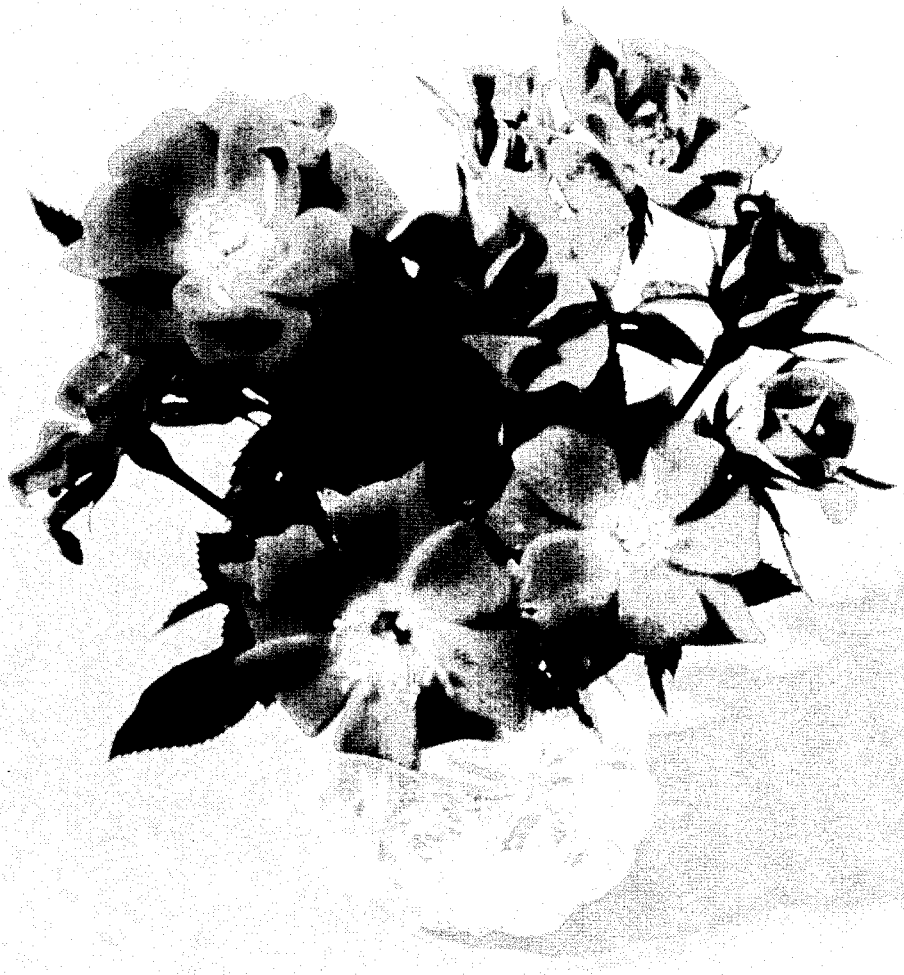

* * * * *